United States Patent [19]
Murray

[11] 3,960,147
[45] June 1, 1976

[54] COMPRESSION BONE STAPLES AND METHODS OF COMPRESSING BONE SEGMENTS

[76] Inventor: William M. Murray, 109 Wynnwood Drive, Pittsburgh, Pa. 15215

[22] Filed: Mar. 10, 1975

[21] Appl. No.: 556,580

[52] U.S. Cl. .............................. 128/92 B; 85/49; 72/454
[51] Int. Cl.² ........................................ A61F 5/04
[58] Field of Search ............. 128/92 R, 92 B, 92 E, 128/92 EA, 83, 335, 337, 334; 85/49, 13; 29/238; 72/454, 409

[56] References Cited
UNITED STATES PATENTS

| | | | |
|---|---|---|---|
| 733,723 | 7/1903 | Lukens | 128/337 |
| 1,728,316 | 9/1929 | Wachenfeldt | 128/334 R |
| 2,132,295 | 10/1938 | Hawkins | 85/13 |
| 2,811,073 | 10/1957 | Klopstock | 85/49 |
| 3,446,212 | 5/1969 | Le Roy | 128/337 X |
| 3,601,127 | 8/1971 | Finegold | 128/337 |
| 3,807,394 | 4/1974 | Attenborough | 128/92 B |

Primary Examiner—John D. Yasko
Attorney, Agent, or Firm—Buell, Blenko, and Ziesenheim

[57] ABSTRACT

An apparatus and method are provided for placing adjacent bone ends under end to end compression using a staple having spaced apart prongs adapted to be forced into adjacent bone ends, said prongs being connected at one end by a head member having at least two spaced apart transverse ribs, removably engageably by a drive means for inserting the prongs in the bone ends and then forcing the ribs of the head member together to urge the prongs together and toe them in.

8 Claims, 10 Drawing Figures

COMPRESSION BONE STAPLES AND METHODS OF COMPRESSING BONE SEGMENTS

This invention relates to compression bone staples and methods of compressing bone segments and particularly to a bone staple and staple tool and methods of compressing small bones and bone fragments together.

There are numerous orthopedic operative procedures in which it would be useful to have available a tool and method which could be used to draw small bones or bone fragments together under compression. For example, one such well known operative procedure is arthrodesis in the foot or wrist. This is a procedure in which the small bones are held together to cause fusion of the bones. Another procedure where such an apparatus and method would be helpful is the procedure known as osteotomy. Prior to this invention there has been available no practical mechanism for fastening and then pressurizing the ends of small bones together to promote fusion. Heretofore staples or other fasteners have been used but there has been no way in which they could be compressed after insertion to assure the bone end pressure necessary for rapid and reliable fusion. The result has been that in many cases the operation must be repeated until fusion is accomplished.

I have discovered an apparatus and method of compressing bone ends which simplifies this procedure and makes compression assured.

The present invention provides in combination a staple having spaced apart prongs adapted to be forced into adjacent bone ends, said prongs connected by a head member having at least two spaced apart transverse ribs or corrugations and a drive means or tool engaging said corrugations to hold the staple during driving, and means on said tool forcing said corrugations toward one another after the staple is in place so as to urge the prongs together thereby applying pressure between said bone ends. Simultaneously with bringing the prongs closer together by the crimping action described, the prong tips are forced to "toe in" so as to prevent staple dislodgment. Preferably the two corrugations have a right angle side remote from each other and the tool has a recess engaging said side on the outside and a finger member engaging said corrugation on the inside. Preferably the tool has a screw operated scissor mechanism acting on the staple head to compress it.

In the foregoing general disclosure of my invention I have set out certain objects, purposes and advantages of this invention. Other purposes, objects and advantages will be apparent from a consideration of the following description and the accompanying drawings in which.

Figure 1:
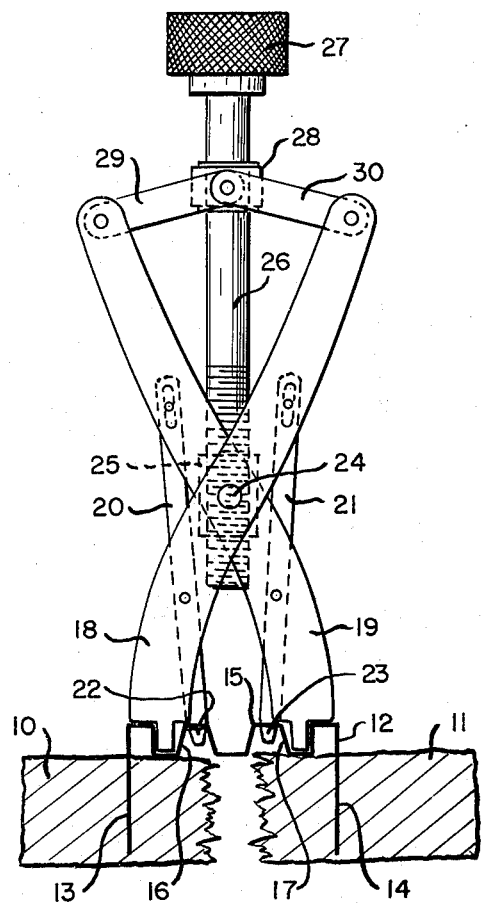
FIG. 1 is a side elevational view of a presently preferred form of staple and tool of this invention in the normal position for insertion in a pair of bone ends.
Figure 2:
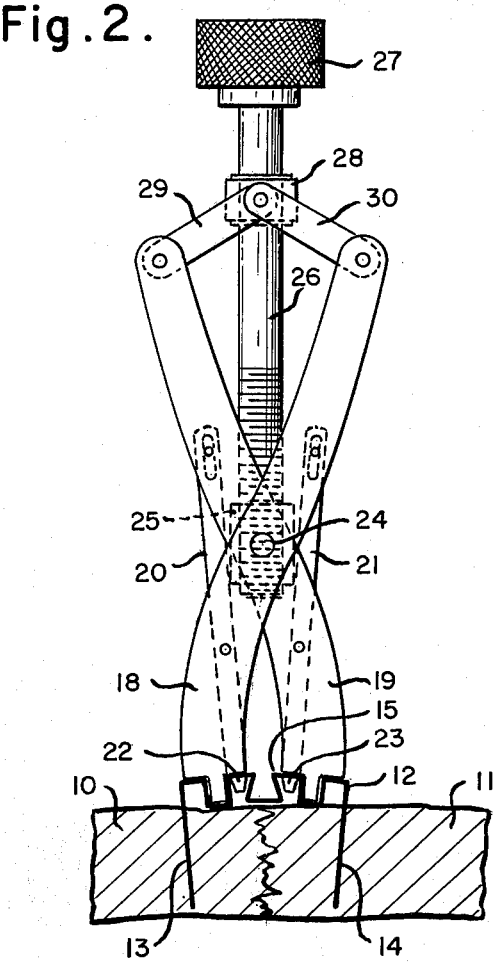
FIG. 2 is a side elevational view of the staple and tool of FIG. 1 in the compressed position.
Figure 3A:
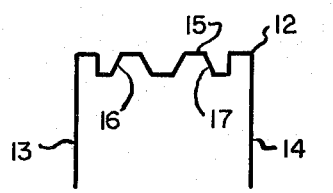
FIGS. 3a and 3b are side elevational views of a second embodiment of staple in the normal and compressed condition.
Figure 4A:
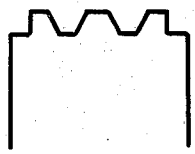
FIGS. 4a and 4b are side elevational views of a third embodiment of staple in the normal and compressed condition.
Figure 5A:
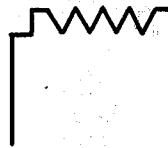
FIGS. 5a and 5b are side elevational views of a fourth embodiment of staple in the normal and compressed condition.
Figure 6A:
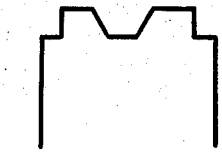
FIGS. 6a and 6b are side elevational views of a fifth embodiment of staple in the normal and compressed condition.
Figure 3B:
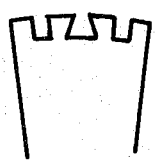
Figure 4B:
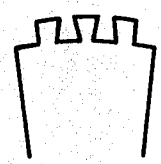
Figure 5B:
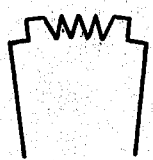
Figure 6B:

Referring to the drawings I have illustrated in FIGS. 1 and 2 a pair of bone ends 10 and 11 which are to be brought into end to end compression. A staple 12 having spaced prongs 13 and 14 connected by a head member 15 having spaced apart corrugations 16 and 17 is fixed to tool scissor legs 18 and 19 by holding arms 20 and 21 pivoted to the legs 18 and 19 and having transverse fingers 22 and 23 engaging within the corrugations 16 and 17. The scissors legs 18 and 19 are pivoted on pin 24 fixed in nut 25. A screw 26 having a turning knob 27 is threaded at its other end in nut 25. A sleeve 28 is mounted on screw 26 intermediate its ends and carries links 29 and 30 pivoted at one end thereto. The other ends of links 29 and 30 are pivotally connected to the ends of legs 18 and 19.

Rotation of screw 26 by means of knob 27 causes the legs 18 and 19 to pivot together folding the head 15 of staple 12 and causing the prongs 13 and 14 to be brought together thus placing the bone ends 10 and 11 under end to end compression as shown in FIG. 2. Toeing in of the prong tips occurs as the ends of legs 18 and 19 become nonparallel when coming together as shown in FIG. 2. Disengagement of the driver-compressor tool from the staple is then accomplished by turning its knob 27 backwards slightly and sliding the tool off the staple.

In FIGS. 3, 4, 5 and 6 I have illustrated various forms of staple which might be used in this invention. It is obvious that other forms of staple might be used so long as appropriate corrugations or folds are provided for engagement by the scissor leg arrangement.

In the foregoing specification I have set out certain preferred embodiments and practices of my invention, however, it will be understood that this invention may be otherwise embodied within the scope of the following claims.

I claim:

1. An apparatus for placing adjacent bone ends under end to end compression comprising in combination a staple having spaced apart prongs adapted to be forced into adjacent bone ends, said prongs connected by a head member having at least two spaced apart transverse ribs, drive means engaging said ribs to hold the staple during insertion of the prongs into the bone ends to be compressed and means on said drive means forcing said ribs toward one another after said staple is in place so as to urge the prongs together and toe them in.

2. An apparatus as claimed in claim 1 wherein the drive means is a pair of scissor legs pivoted together intermediate their ends, gripping means at one end of said legs engaging said ribs and link means at the other end of said legs acting on said legs to cause them to pivot relatively to one another.

3. An apparatus as claimed in claim 2 wherein the gripping means includes a notched portion on the said one end of said legs engaging the ribs on the head member and removable finger members engaged beneath the ribs.

4. An apparatus as claimed in claim 2 wherein the link means are connected to a screw operator moving said links toward and away from the scissor leg ends to cause the scissor legs to pivot.

5. A tool for crimping staples having spaced prongs connected by a header member having spaced apart collapsible ribs comprising a pair of scissor legs pivoted together intermediate their ends, gripping means at one end of said legs engaging said collapsible ribs and link means at the other end of said scissor legs acting on said legs to cause them to pivot relative to one another.

6. A tool as claimed in claim 5 wherein the gripping means includes a notched portion on the said one end of said legs engaging the ribs on the head member and removable finger members engaged beneath the ribs.

7. A tool as claimed in claim 5 wherein the link means are connected to a screw operator moving said links toward and away from the scissor leg ends to cause the scissor legs to pivot.

8. The method of connecting and compressing bone ends together comprising the steps of:
   a. inserting the spaced prongs of a two pronged staple having a head member with a collapsible rib connecting said prongs; and
   b. collapsing said rib sides toward one another to cause the prongs to move toward one another and compress the bone ends.

* * * * *